US011280921B2

(12) United States Patent
Niu et al.

(10) Patent No.: US 11,280,921 B2
(45) Date of Patent: Mar. 22, 2022

(54) TIME-CORRECTION DEVICE FOR PET SYSTEM

(71) Applicant: RAYCAN TECHNOLOGY CO., LTD. (SU ZHOU), Suzhou (CN)

(72) Inventors: Ming Niu, Suzhou (CN); Tong Liu, Suzhou (CN); Qingguo Xie, Suzhou (CN)

(73) Assignee: RAYCAN TECHNOLOGY CO., LTD (SU ZHOU), Suzhou (CN)

( * ) Notice: Subject to any disclaimer, the term of this patent is extended or adjusted under 35 U.S.C. 154(b) by 423 days.

(21) Appl. No.: 16/479,880

(22) PCT Filed: Aug. 28, 2017

(86) PCT No.: PCT/CN2017/099237
§ 371 (c)(1),
(2) Date: Jul. 22, 2019

(87) PCT Pub. No.: WO2018/133412
PCT Pub. Date: Jul. 26, 2018

(65) Prior Publication Data
US 2021/0356610 A1    Nov. 18, 2021

(30) Foreign Application Priority Data
Jan. 22, 2017    (CN) .......................... 201710047338.6

(51) Int. Cl.
*G01T 1/29*    (2006.01)
*A61B 6/03*    (2006.01)

(52) U.S. Cl.
CPC ............ *G01T 1/2985* (2013.01); *A61B 6/037* (2013.01)

(58) Field of Classification Search
CPC .............................. G01T 1/2985; A61B 6/037
See application file for complete search history.

(56) References Cited

U.S. PATENT DOCUMENTS

| 8,089,043 B2 | 1/2012 | Casey et al. | |
| 2006/0102845 A1* | 5/2006 | Williams | G01T 1/2985 |
| | | | 250/363.03 |

(Continued)

FOREIGN PATENT DOCUMENTS

| CN | 102783964 A | 11/2012 |
| CN | 103976755 A | 8/2014 |

(Continued)

*Primary Examiner* — Hugh Maupin
(74) *Attorney, Agent, or Firm* — William H. Honaker; Dickinson Wright PLLC

(57) ABSTRACT

A time correction device for a PET system comprises a detector ring, a ring-shaped prosthesis, and detection, data acquisition, data coincidence, time shift calculation, data correction application modules. Center of the ring-shaped prosthesis overlaps with axial and radial center of the detector ring. The detection module is located in ring-shaped prosthesis. Center of the detection module is at the center of the ring-shaped prosthesis. The data acquisition module comprises data gathering and energy filtering modules connected to each other. The data gathering module comprises detectors and the detection module. The energy filtering module connects to the data gathering module receiving single-event time information. The data coincidence module is connects to the energy filtering module receiving the single-event time information. Time shift calculation module connects to the data coincidence module providing a shift value of the detectors. The data correction application module applies the shift value to the PET system.

10 Claims, 4 Drawing Sheets

(56) References Cited

U.S. PATENT DOCUMENTS

| | | | |
|---|---|---|---|
| 2007/0131857 A1* | 6/2007 | Thompson | G01T 1/2985 |
| | | | 250/252.1 |
| 2015/0065869 A1 | 3/2015 | Daghighian et al. | |
| 2018/0021009 A1* | 1/2018 | Ye | A61B 6/037 |
| | | | 250/252.1 |

FOREIGN PATENT DOCUMENTS

| CN | 104434160 A | 3/2015 |
|---|---|---|
| CN | 104977601 A | 10/2015 |
| CN | 10623336 A | 12/2016 |

* cited by examiner

TIME-CORRECTION DEVICE FOR PET SYSTEM

CROSS-REFERENCE TO RELATED APPLICATION

This application is a 35 U.S.C. § 371 national stage application of PCT Applicaton Serial No. PCT/CN2017/099237 filed on Aug. 28, 2017, which claims priority to Chinse Patent Application Ser. No. CN201710047338.6 filed on Jan. 22, 2017, the entire disclosure of which are considered as part of the disclosure of this application and are hereby incorporated by reference.

FIELD OF THE INVENTION

The present application relates to a time correction device in the field of medical devices, M particular to a time correction device for a PET system.

BACKGROUND OF THE INVENTION

Positron Emission Tomography (PET) system is a non-invasive molecular imaging device for functional metabolism, the principle of which is read as: radioactive nuclide decay produces positrons which will annihilate through combination with the electrons in a tissue after moving a short distance (usually a few millimeters), and the mass of which is converted into a pair of gamma photons that emit energy of 0.51.1 MeV in the opposite direction respectively; Doctors are thereby assisted in making relevant diagnoses for diseases by means of using the positron nuclides labeled on a molecular probe as tracers, acquiring time, energy and position information of the gamma photons generated from the annihilations of the positrons through detecting, obtaining Line of Response (also referred to as LOR) to the annihilation events by using coincidence technique, and then adopting an image reconstruction algorithm for imaging to reflect the degree of ingestion of the tracer at each part of body.

The coincidence time resolution is an important indicator of the PET system. It expresses the uncertainty of the arrival of a pair of gamma photons after the annihilation event in the PET system, which is also known as response fluctuation. From the definition of time resolution, we can know that the response line will increase accordingly in the detector design using a crystal array. Each response line corresponds to a time spectrum. The time spectra corresponding to many response lines are combined into the time spectrum of the basic unit module. There is a uniformity error between the crystal strips in the crystal array, that is, performance difference between the crystal strips in the crystal array (including light output, decay time constant, photon transit time, etc.), and a nonlinear relationship in the region of the photoelectric conversion device, as a result, none of the center values of the time spectra is exactly at an ideal zero time, and thus, the width of the time spectrum of the basic unit module is broadened.

In the prior art the direct measurement correction method for time correction is adopted by most PET, wherein the rotating rod source time correction method is more classic. The rotating rod source time correction method utilizes a rod source used in transmission scanning, collects coincidence data and performs iterative processing, etc. for time correction while the rod source is doing circular motion around the detector ring for decay correction. Referring to Williams J, Lao D, K. L M, et al, Crystal-based coincidence timing calibration method, U.S. Pat. No. 7,030,382 B2, this method utilizes the decay correction rod source in a classic PET to carry on the correction without the need for additional equipment for classic clinical PET instruments. Nowadays, PET/CT is gradually popular in the market. PET/CT directly refers to the density information of the imaging tissue reflected by CT image and thus generates the decay factor required for PET decay correction, which makes most new instruments no longer rely on rotating rod sources when making decay corrections and further makes this method face a certain challenge in PET/CT state.

Some direct measurement correction methods are also provided for time correction by using an iterative calculation method after data are acquired by placing a solid line source, a rod source or a tracer injected cylindrical prosthesis or ring-shaped prosthesis in the center of a detector ring (See Willians J. Automated coincidence timing calibration for a pet scanner, U.S. Pat. No. 5,272,344 A, and Xiaoli Li, Burr, K. C, Gin-Chung Wang, Huini Du, etc. Timing calibration for time-of-flight PET using, positron-emitting isotopes and annihilation targets, IEEE Nucl, Sci. Symp. Conf. Rec., pp. 1-5, 2013). When a line source, a column source, or a tracer injected cylindrical prosthesis in a small diameter is used, only a few response lines can be involved when time correction is carried on. That is to say, time information correction is conducted on part of the detectors on the ring. By contrast, when a radioactive cylindrical prosthesis in a large diameter is used and meanwhile the time distribution information is acquired from enough response lines, the time distribution on most response lines is diffused and there is a relatively large error for the confirmation of their center offset time due to the large volume of the cylindrical prosthesis.

In addition, from the perspective of the complexity of the system, the rotation of a rod source according to the rotating rod source time correction method requires the use of additional mechanical transmissions, for example, a motor is used to control and adjust the position of the rod source in order to achieve precise control, which leads to certain difficulties in design and implementation of the mechanical components and increases the complexity of the entire PET system. Rotating rod source time correction method mostly uses an iterative algorithm with a large amount of basic data and a high algorithm complexity of $O(n^2)$. $O(n^2)$ is of square order and herein refers to the statement execution times in the algorithm, wherein n means each basic unit and can also be understood as the number of crystal lattices. The iterative algorithm takes relatively long operation time to obtain the final result. The rotating rod source generally adopts 68-Ge which has a half-life period of 270.95 days. Thus, the Ge source needs to be replaced after a certain time, which directly increases the operation cost of PET.

When a line source, a column source, or a tracer injected cylindrical prosthesis in a small diameter is used as the basis of correction, only a few response lines can be involved when correction although the correction device used is rather simple. That is to say, time information correction is only conducted to some of the response lines on the ring without covering all the response lines over a full field of view (FOV). By contrast, when a radioactive cylindrical prosthesis in a large diameter is used and meanwhile the time distribution information is acquired from enough response lines, the time distribution on most response lines is diffused and the full width at half maximum of the time distribution increases, which leads to failure to correct the time offset of all response lines in the field of view accurately, due to the large volume of the cylindrical prosthesis.

Some PET systems are provided that the ring-shaped prosthesis is placed at the center of their detector rings. Similar to the method of using rotating rod source, a complex iterative algorithm is used to obtain the final correction result, of which computational complexity is high, is $O(n^2)$ and leads to relatively long operation time although its acquisition time is short. Thus, in order to speed up the operation in practical applications, an additional high-performance computing server is required and the cost of the PET system is increased.

In addition to the above methods, a method using a time probe is also provided for time correction, which fixes the radioactive source and the crystal together onto the center of the FOV as a reference to obtain the time shifts between it and each module. However, its correction unit is mostly a basic module and is not accurate to the minimum basic unit "crystal lattice". Moreover, the radioactive source used for the fixation is 68-Ge which has a half-life period of 270 days or 22-Na which has a half-life period of 2.6 years. That means the radioactive source must be replaced in order to maintain the performance of the PET system after a certain period of time.

In summary, in the prior art, there are problems, such as incomplete correction effect, complicated algorithm, and high equipment cost, etc. when making time correction for PET systems. Therefore, it is desired for today's PET system to find a time correction method with excellent effect, simple and fast operation, low algorithm complexity and low cost.

SUMMARY OF THE INVENTION

The purpose of the present application is to provide a time correction device for a PET system, so as to overcome the problem in the prior art of incomplete correction effect, complicated algorithm, and high equipment cost when making time correction for PET systems.

Thus, a time correction device for a PET system according to the present application is provided, comprising a detector ring which comprises a plurality of detectors arranged in sequence; a ring-shaped prosthesis which is located in the detector ring with its center overlapping with an axial and radial center of the detector ring; a detection module which is located in the ring-shaped prosthesis with its center located at the center of the ring-shaped prosthesis; a data acquiring module which is provided with a data collecting module including the detectors and the detection module and an energy filtering module receiving single-event time information sent from said data collecting module, which are connected with each other; a data coincidence module which is connected to the energy filtering module and receives single-event time information sent from said energy filtering module; a time shift calculation module which is connected to the data coincidence module and obtains shift values of the detectors through the single-event time information; and a data correction application module which is configured to apply the shift values to an entire system to correct single-event time information.

The axial length of the ring-shaped prosthesis does not exceed the axial length of the detector ring, and the outer diameter of the ring-shaped prosthesis does not exceed the inner diameter of the detector ring.

The inner diameter of the ring-shaped prosthesis is between half of the diameter of the detector ring and the outer diameter of the detection module.

The ring-shaped prosthesis is uniform in thickness.

The ring-shaped prosthesis has a radioactive source, and activity of the radioactive source satisfies the condition that an total counting rate of a PET system after the radioactive source is placed is at least twice the counting rate of the PET system under empty scanning.

The activity of the radioactive source in the ring-shaped prosthesis is provided in the range of 30~500 uCi.

The time resolution of the detection module is higher than that of the detectors in the detector ring.

The detection module is provided with high-time performance with a time resolution of less than 1 ns.

The detection module is also provided with a lutetium-yttrium oxy-orthosilicate scintillation crystal, a photoelectric conversion device and an electronic readout section, in which the lutetium-yttrium oxy-orthosilicate scintillation crystal is coupled to the photoelectric conversion device that is connected to the electronic readout section.

The photoelectric conversion device is one selected from the group consisting of a photomultiplier tube, a silicon photomultiplier tube, a multi-pixel photon counter and a Geiger mode avalanche diode.

The data gathering module acquires tabular single-event time information through the detectors in the detector ring and the detection module, and the energy filtering module analyzes and filters the single-event time information collected by the data gathering module through a certain energy window and filter out scattering events.

The present application adopts a ring-shaped prosthesis instead of using a rotating rod source, which greatly reduces the design of the PET system and controls the complexity of the design of PET system. Moreover, the use of the ring-shaped prosthesis for time correction operation also has an advantage of easy operation, and is thus better adapted to popular PET or PET/CT instruments today. The present application places a detection module into the center of the field of view as a time reference to the detectors in the detector ring so that the complexity of algorithm is reduced through the method of using the same reference. The present application just needs to collect data once statically when correction, and thus the algorithm is fast and efficient, which reduces the complexity and the computation time compared with the iterative optimization correction algorithm heavily used in the prior art.

BRIEF DESCRIPTION OF THE DRAWINGS

These and other features and advantages of this application will become more apparent to those skilled in the art from the detailed description of preferred embodiment. The drawings that accompany the description are described below.

DESCRIPTION OF THE PREFERRED EMBODIMENTS

The followings are used to further illustrate the present application with specific embodiments. It should be understood that the following embodiments is only used to explain the present application but not to limit the scope of the present application.

Figure 1:
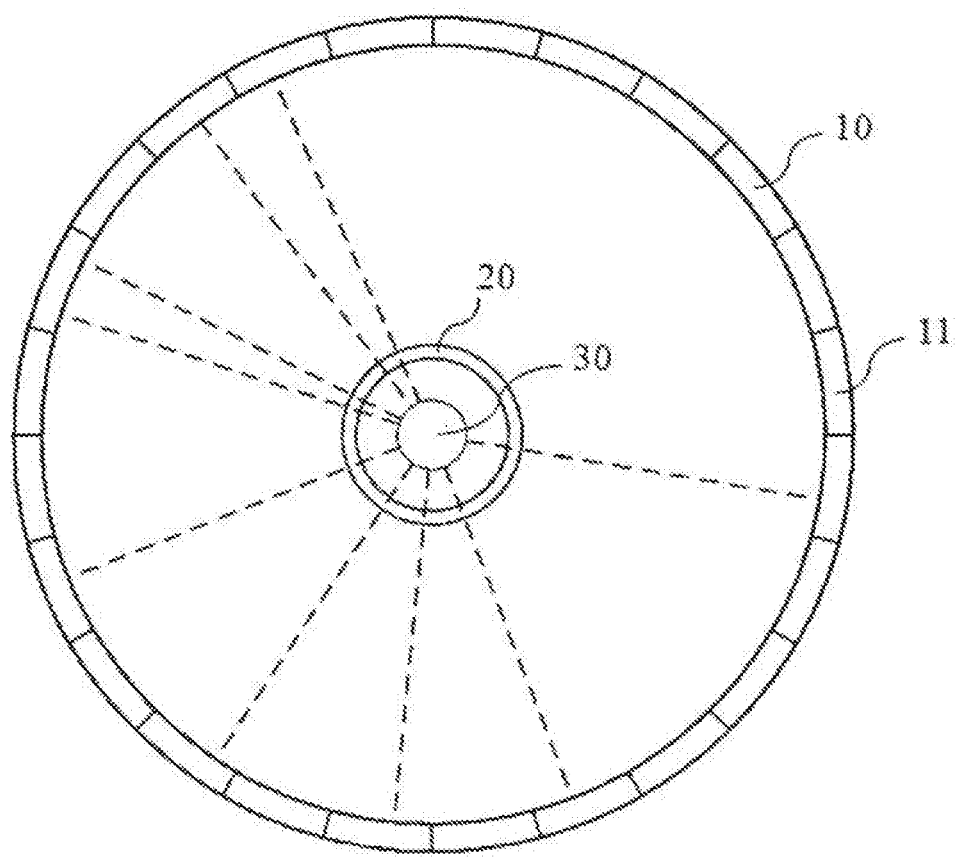
FIG. 1 is a schematic diagram showing an arrangement of a time correction device for a PET system in accordance with a preferred embodiment of the present application.

FIG. 1 is a schematic view showing an arrangement of a time correction device for a PET system provided by the present application. The time correction device comprises a detector ring 10, a ring-shaped prosthesis 20 and a detection module 30. The detector ring 10 is composed of a plurality of detectors 11 which are arranged in sequence to form a ring. The ring-shaped prosthesis 20 is located inside the detector ring 10 with its center overlapping with the axial and radial center of the detector ring 10. The detection module 30 is located inside the ring-shaped prosthesis 20 with its center located at the center of the detector ring 10 and the ring-shaped prosthesis 20. The axial length of the ring-shaped prosthesis 20 does not exceed the axial length of the detector ring 10, the outer diameter of the ring-shaped prosthesis 20 does not exceed the inner diameter of the detector ring 10, and the inner diameter of the ring-shaped prosthesis 20 is not less than the outer diameter of the detection module 30. Preferably, the inner diameter of the ring-shaped prosthesis 20 is between the half of the diameter of the detector ring 10 and the diameter of the detection module 30. The ring-shaped prosthesis 20 is uniform in thickness and is not easy to be deformed. In order to avoid background and random noise interference, radioactive source needs to be injected into the ring-shaped prosthesis 20 for making correction. The activity of radioactive source is preferably defined so that an overall counting rate of a PET system after setting the radioactive source is at least twice or higher, preferably 10 times higher than the counting rate of the PET system under empty scanning. The radioactive source inside the ring-shaped prosthesis 20 is a liquid positron source commonly used in PET systems, such as, $^{18}$F-FDG, $^{18}$FDOPA, $^{18}$F-FLT, etc. based on $^{18}$F, $^{15}$O—H$_2$O based on $^{15}$O, $^{11}$C-sodium acetate, 11C-choline, etc. based on $^{11}$C. The higher the sensitivity of the instrument, the lower the activity required, thus the activity of the radioactive source in the ring-shaped prosthesis 20 of the present application is preferably 30 to 500 uCi, and more preferably 300 to 500 uCi with low cost and good flexibility.

In the embodiment of FIG. 1, the shape of the detector ring 10 is circular ring-shaped. It is contemplated for skilled person in the art that the detector ring according to the present application is not limited to be circular ring-shaped and can also be different ring-shaped or even not ring-shaped detectors. For example, the detectors of detector ring 10 can be arranged in a form of flat plate, quadrangle or octagon. The detection module 30 in the PET system of the present application adopts a detection module with high time performance. It should be understood that, if the time performance of the detection module 30 is better than the inherent time performance of the detector 11 on the detector ring 10, that is, the time resolution of the detection module 30 is higher than that of the detector 11 on the detector ring 10, the detection module 30 can be considered to be with high time performance in the present application. Meanwhile, due to the difference between various PET instruments clinically in their time resolution, the high time performance of detection module in the present application is less than 1 ns. In addition, compared with the ring-shaped prosthesis 20, the detection module 30 itself is rather small, which may be of other shapes and not limited to a circular shape.

Figure 2:
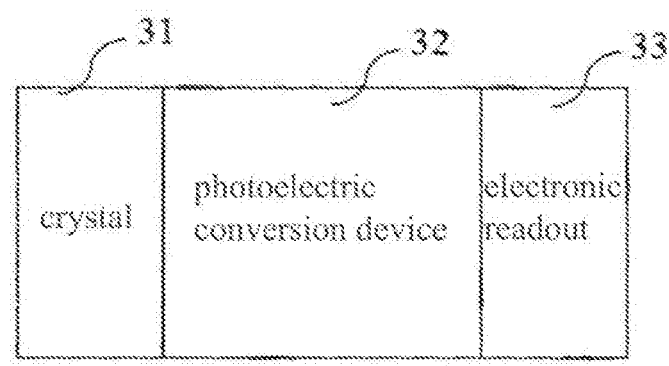
FIG. 2 is a schematic diagram showing the structure of a detection module of a time correction device for a PET system in accordance with a preferred embodiment of the present application.

FIG. 2 is a schematic diagram showing the structure of a detection module 30 of a time correction device for a PET system in accordance with a preferred embodiment of the present application. The detection module 30 includes a lutetium-yttrium oxy-orthosilicate scintillation crystal 31 (referred to as LYSO crystal), a photoelectric conversion device 32 and an electronic readout section 33. The LYSO crystal 31 is coupled to the photoelectric conversion device 32. The photoelectric conversion device 32 is connected to the electronic readout section 33. The connection of the electronic readout section 33 and the data collection section (not shown) belongs to common sense of this field. In a preferred embodiment of the present application, the photoelectric conversion device 32 adopts a photomultiplier tube (PMT) with a model number of Hamamatsu R9800 in the embodiment of FIG. 2, for example.

Figure 3:
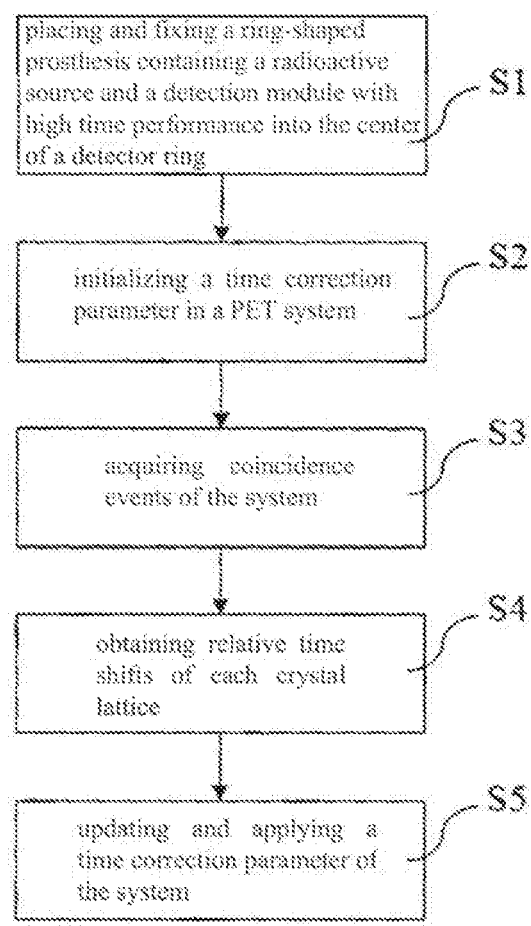
FIG. 3 is a flow diagram of a time correction device for a PET system in accordance with a preferred embodiment of the present application.

FIG. 3 is a flow diagram of a time correction device for a PET system in accordance with a preferred embodiment of the present application. The steps of use of the time correction device of the present application are as follows:

Step S1: placing and fixing a ring-shaped prosthesis 20 containing a radioactive source and a detection module 30 into a detector ring Step S2: initializing a time correction parameter in a PET system;

Step S3: acquiring coincidence events of the system;

Step S4: obtaining relative time shifts of each crystal lattice;

Step S5: updating and applying a time correction parameter of the system, wherein, the acquisition of coincidence events in step S3 is specifically to acquire coincidence events of respective crystal lattices with respect to the central detection module 30, so as to at least acquire accurate time information and crystal lattice position information including the arrival of the event. It should be understood that the crystal lattice in the detector is determined by the crystal array specification used in a design for detectors, which is not specifically defined herein. The step S3 is different from the prior art in that not only the coincidence data of the detector ring 10 itself but also the coincidence data between the detector ring 10 and the detection module 30 in the center of the detector ring 10 is collected in the step S3 of the present application.

In step S4, a coincidence time distribution is acquired from the coincidence events obtained by respective crystal lattices in the detector ring 10 with respect to the detection module 30 and thereby relative time shifts $t_n$, are obtained, in which n is a crystal lattice number and a positive integer. Compared with the method of using an iterative algorithm to correct parameters in the conventional technique, the step S4 of the present application provides a direct measurement calculation method to obtain time shift for each crystal lattice and then obtains a correction parameter, which leads to a high-speed, simple and effective algorithm and therefore the complexity and computing time are dramatically decreased.

In step S5, the obtained relative time shifts $t_n$ of respective crystal lattices are applied to the system. The time information in the original data is corrected during acquiring a single event. Namely, the obtained relative time shifts $t_n$, are subtracted or added depending upon the calculation method of the relative time shifts into the original time information. There are two ways to calculate the relative time shills. The first one is t-center—t-ring wherein the correction calculation is to add relative time shifts $t_n$. The second one is t-ring—t-center wherein the correction calculation is to subtract relative time shifts $t_n$.

Figure 4:
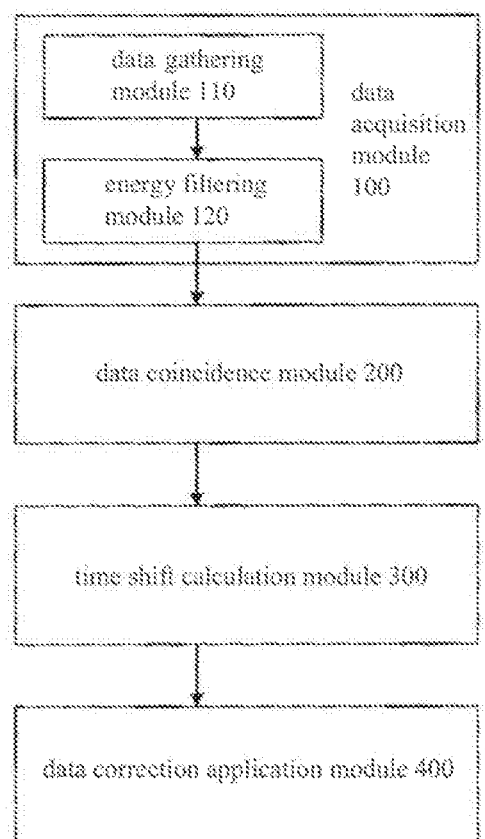
FIG. 4 is a system diagram of a time correction device for a PET system in accordance with a preferred embodiment of the present application.

FIG. 4 is a system diagram of a time correction device for a PET system in accordance with a preferred embodiment of the present application. As can be seen from FIG. 4, the system of the time correction device provided by the present application includes a data acquisition module 100, a data coincidence module 200, a time shift calculation module 300 and a data correction application module 400. The data acquisition module 100 includes a data gathering module 110 and an energy filtering module 120 connected to each other, wherein the energy filtering module 120 is connected to the data coincidence module 200 and transmits the collected single-event time information to the data coincidence module 200.

The data acquisition module 100 is configured to acquire single-event time information of each detector on the detection module and the detector ring and to preprocess partially the single-event time information by using a energy window. The data gathering module 110 is used to acquire the tabular single-event time information of each detector on the detection module and the detector ring and then transmit and store it into an upper computer server for processing. The energy filtering module 120 is used to analyze and filter the original single-event time information collected by the data gathering module 110 through a certain energy window and finally filter out scattering events. For example, in the embodiment of FIG. 1, the data gathering module 110 is the sum of the detectors in the detector ring 10 and the detection module 30. The data gathering module 110 acquires the tabular single-event time information generated by detectors 11 of the detector ring 10 and the detection module 30. The data gathering module 110 transmits and stores the above single-event time information into the upper computer server for processing through connection with the energy filtering module 120. The energy filtering module 120 in the upper computer server analyzes and filters the original single-event time information collected by the data gathering module 110 through a certain energy window and finally filter out scattering events. It should be understood that the selection of the energy window can be determined by a person skilled in the art according to the needs for specific information collection.

It should be noted that the arrangement sequence of the data gathering module 110 and the energy filtering module 120 in the data acquisition module 100 can be reversed in present application. The energy filtering module 120 can be integrated in the respective detectors 11 on the detector ring 40 and the detection module 30 so that the scattering events can be filtered out through the energy filtering module 120 and then single-event time information is uploaded to the upper computer server through the data gathering module 110. The data collection efficiency is higher in that mode when activity of radioactive source is relatively high.

The data conforming module 200 is used to perform data coincidence operations on the single-event time information acquired by the data acquiring module 100 according to the set time window and other conditions so as to obtain coincidence data of each crystal lattice on each detector relative to the detection module. For example, the energy filtering module 120 sets several different filtering ranges, such as 350-650 keV, 250-750 keV, etc. The data coincidence module 200 performs data coincidence accordingly and obtains coincidence data of each crystal lattice of each detector on the detector ring 10 relative to the detection module 30 with high time performance.

The time shift calculation module 300 is configured to acquire time distribution for the coincidence data of each crystal lattice relative to the detection module, and to obtain its shift values $t_n$, wherein n is a crystal lattice number and is a positive integer.

The data correction application module 400 is configured to apply the obtained shift values $t_n$, of the respective crystal lattices to the entire system and to perform time correction operations on the time information in each acquired single event. Specifically, time information correction is performed on the time information in tabular single-event time information acquired by the data acquisition module 100 by removing the obtained shift values $t_n$. The calculation method and the correction method of the shift values $t_n$ are mentioned as the above step S5.

Figure 5:
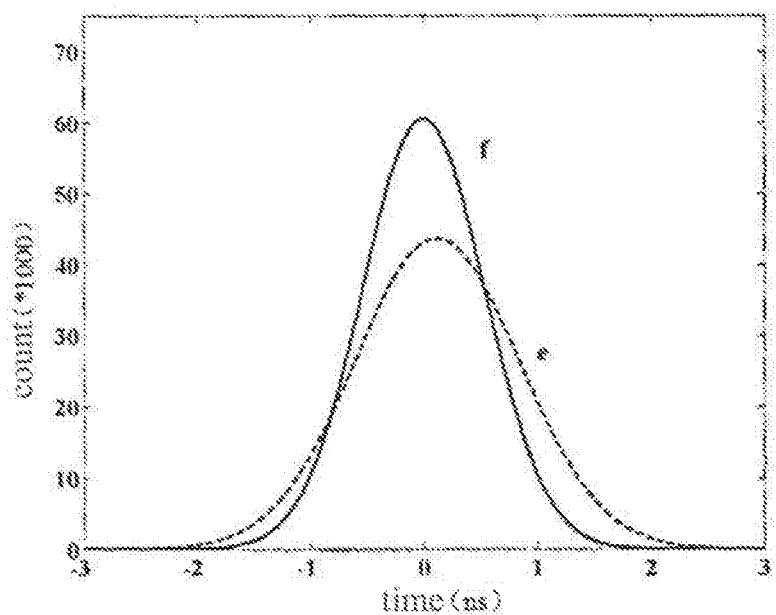
FIG. 5 is a schematic diagram showing time distribution of a time correction device for a PET system in accordance with a preferred embodiment of the present application.

FIG. 5 is a schematic diagram showing time distribution of a time correction device for a PET system in accordance with a preferred embodiment of the present application. A broken line e represents time distribution of a system composed of all detectors in the detector ring 10 before time correction, in which the time resolution of is 1.7 ns and the center value is 121.8 ps. A solid line f represents time distribution of a system composed of all detectors after time correction, in which the time resolution is 1.26 ns and the center value is −3.6 ps. Apparently, the time resolution according to the present application is more advantageous to the implementation of TOF-PET technology (time-of-flight PET technology) relative to the time resolution of 400-500 ps in the prior art.

Figure 6:
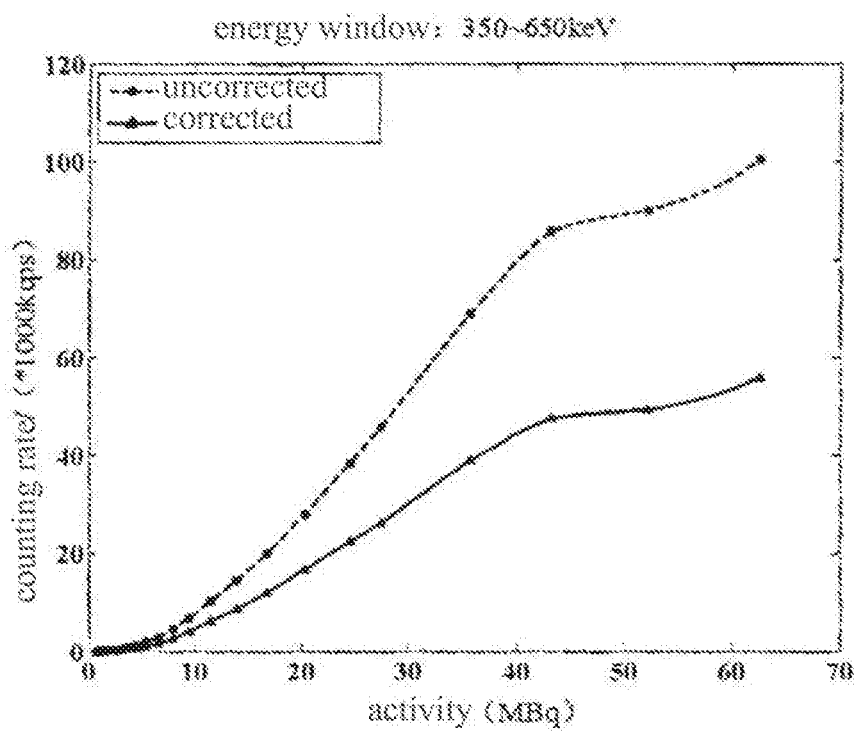
FIG. 6 is a schematic diagram showing a comparison of random coincidence for a time correction device for a PET system in accordance with a preferred embodiment of the present application, in which a broken line represents that no time correction is made, and a solid line represents that time correction is made.
Figure 7:
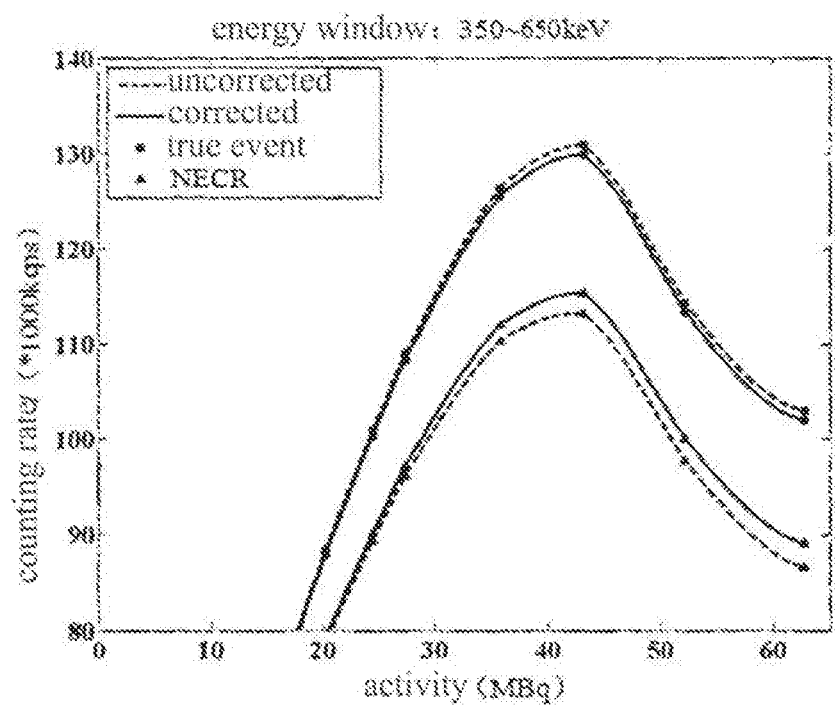
FIG. 7 is a schematic diagram showing a comparison of NECR curve for a time correction device for a PET system in accordance with a preferred embodiment of the present application, in which a broken line represents that no time correction is made, and a solid line, represents that time correction is made.

FIGS. 6 and 7 respectively show a random coincidence and a NECR curve distribution before and after time correction of the system. FIG. 6 is a schematic diagram showing a comparison of random coincidence for a time correction device for a PET system in accordance with a preferred embodiment of the present application, in which a broken line represents that no time correction is made and a solid line represents that time correction is made. FIG. 7 is a schematic diagram showing a comparison of NECR curve for a time correction device for a PET system in accordance with a preferred embodiment of the present application, in which a broken line represents that no time correction is made and a solid line represents that time correction is made. The random coincidence event will decrease with the decrease of time window, and the size of the time window is determined upon time resolution which is generally twice the time resolution. The small quantity of random coincidence events which is reflected in the final imaging indicates that image quality(signal-to-noise ratio) will be improved. The NECR curve is obtained by testing the NECR prosthesis according to the method used in the NEM ANU4 standard. It can be seen from FIG. 6 that the random coincidence distribution after the use of time correction is lower than before. Moreover, it can be seen from FIG. 7 that NECR gets a large boost before and after time correction almost without much change in the true event. The range of improvement can be seen from FIG. 6. The counting rate is nearly reduced by half over the entire activity range.

The present application adopts a ring-shaped prosthesis instead of a rotating rod source, which greatly reduces the needs of design of PET system and allows the complexity of the design of PET system to be controllable. Moreover, the use of the ring-shaped prosthesis for time correction operation make it easy to operate, and is thus better adapted to popular PET or PET/CT instruments today.

The present application introduces a detection module, in particular, a detection module with high time performance to be placed into the center of the field of view as a time reference to the detectors in the detector ring. Therefore the complexity of algorithm is reduced through the method of using the same reference. In addition, the present application just needs to collect data once statically when correction and let the time complexity at this moment be known as O(n), wherein n is the total number of crystal lattices on the detector ring. The algorithm is fast, simple and efficient so as to reduce the complexity and the computation time compared with the iterative optimization correction algorithm heavily used in the prior art.

The present application can also involve making crystal time correction for the smallest detection unit on the detector ring namely, the small crystal lattice. The calculation correction efficiency can be improved by using that calculation method.

The foregoing application has been described in accordance with the relevant legal standard, thus the description is exemplary rather than limiting in nature. Variations and modifications to the disclosed embodiment may become apparent to those skilled in the art and do come within the scope of the application. For example, the structure of the detection module 30 in the present application may be a CZT detector readout through crystal/photoelectric conversion device/electronic, crystal/photoconductive/photoelectric conversion device/electronic, or photoelectric conversion device/electronic. According to another example, the crystal used in the detection module with high-time performance of the present application may be in various kinds such as $LaBr_3$, LSO, LYSO, LuNAP, $BaF_2$, GSO, LFS or $LuI_3$ etc., and the shape of it may be cylindrical, elongated, tapered, and the like. For yet another example, the photoelectric conversion device used in the detection module with high time performance of the present application may be a photomultiplier tube, a silicon photomultiplier (SiPM), a multi-pixel photon counter (MPC), a Geiger-mode avalanche photodiode (G-APD), etc., as long as the transit time distribution (TTS) is less than 500 ps. Accordingly, the scope of legal protection, afforded this application can only be determined by studying the following claims.

What is claimed is:

1. A time correction device for a PET system, comprising:
    a detector ring configured to have a plurality of detectors arranged in sequence;
    a ring-shaped prosthesis located inside of said detector ring with center of said ring-shaped prosthesis overlapping with axial and radial center of said detector ring;
    a detection module located inside of said ring-shaped prosthesis with center of said detection module located at said center of said ring-shaped prosthesis;
    a data acquiring module configured to be provided with a data collecting module including said detectors and said detection module and an energy filtering module receiving single-event time information sent from said data collecting module, which are connected with each other;
    a data coincidence module configured to connect to said energy filtering module and receive single-event time information sent from said energy filtering module;
    a time shift calculation module configured to connect to said data coincidence module and obtain shift values of said detectors through said single-event time information; and
    a data correction application module configured to apply said shift values to said PET system to correct single-event time information.

2. The time correction device for a PET system according to claim 1, wherein said ring-shaped prosthesis is provided with an axial length which does not exceed an axial length of said detector ring and an outer diameter which does not exceed an inner diameter of said detector ring.

3. The time correction device for a PET system according to claim 2, wherein said ring-shaped prosthesis is provided with an inner diameter which is between half of a diameter of said detector ring and an outer diameter of said detection module.

4. The time correction device for a PET system according to claim 1, wherein said ring-shaped prosthesis is uniform in thickness.

5. The time correction device for a PET system according to claim 1, wherein said ring-shaped prosthesis is provided inside with a radioactive source and an overall counting rate of the PET system containing a radioactive source is at least twice the counting rate of the PET system under empty scanning.

6. The time correction device for a PET system according to claim 5, wherein the activity of said radioactive source in said ring-shaped prosthesis is provided in a range of 30~500 uCi.

7. The time correction device for a PET system according to claim 1, wherein at detection module is provided with a time resolution which is higher than that of said detectors in said detector ring.

8. The time correction device for a PET system according to claim 7, wherein said detection module is provided with high-time performance with a time resolution of less than 1 ns.

9. The time correction device for a PET system according to claim 1, wherein said detection module is provided with a lutetium-yttrium oxy-orthosilicate scintillation crystal, a photoelectric conversion device and an electronic readout section, in which the lutetium-yttrium oxy-orthosilicate scintillation crystal is coupled to the photoelectric conversion device that is connected to the electronic readout section.

10. The time correction device for a PET system according to claim 9, wherein said photoelectric conversion device is one selected from a group consisting of a photomultiplier tube, a silicon photomultiplier tube, a multi-pixel photon counter, and a Geiger mode avalanche diode.

* * * * *